United States Patent [19]
Leander

[11] Patent Number: 4,745,126
[45] Date of Patent: May 17, 1988

[54] METHOD OF TREATING ANXIETY WITH TETRAHYDROBENZ[C,D]INDOLE-6-CARBOXAMIDES

[75] Inventor: J. David Leander, Indianapolis, Ind.

[73] Assignee: Eli Lilly and Company, Indianapolis, Ind.

[21] Appl. No.: 25,291

[22] Filed: Mar. 12, 1987

[51] Int. Cl.⁴ .............................................. A61K 31/40
[52] U.S. Cl. .................................................... 514/411
[58] Field of Search ......................................... 514/411

[56] References Cited

U.S. PATENT DOCUMENTS 4,576,959  3/1986  Flaugh ................................ 514/411

FOREIGN PATENT DOCUMENTS 148440  7/1985  European Pat. Off. .
153083  8/1985  European Pat. Off. .

OTHER PUBLICATIONS

The Benzodiazepines, Garattini et al, (1973), pp. 367, 375–376.
Dourish et al., *Trends in Pharmacological Science*, 212–214 (Jun. 1986).
Wuttke et al., *Journal of Pharmacology and Experimental Therapeutics*, 172, 397–405 (1970).
Kilts et al., *Psychopharmacology*, 74, 290–296 (1981).
McCown et al., *Pharmacology, Biochemistry and Behavior*, 18, 277–279 (1983).
Mason et al., *Physchopharmacology*, 92, 30–34 (1987).

*Primary Examiner*—Stanley J. Friedman
*Attorney, Agent, or Firm*—Bruce J. Barclay; Leroy Whitaker

[57] ABSTRACT

The present invention provides a method of treating anxiety in humans employing a 4-substituted-1,3,4,5-tetrahydrobenz[c,d]indole-6-carboxamide derivative.

7 Claims, No Drawings

METHOD OF TREATING ANXIETY WITH TETRAHYDROBENZ[C,D]INDOLE-6-CARBOXAMIDES

BACKGROUND OF THE INVENTION

Extensive research has been conducted for a number of years directed toward the development of compounds capable of treating anxiety in humans which are safer to the user and which exhibit fewer side-effects. For example, several clinically established anxiolytic agents such as the barbituates, meprobamate and the benzodiazepines have numerous side effects such as potential for abuse and addiction or potentiation of the effects of ethanol. The mechanism of action of these compounds is believed to involve the GABA/benzodiazepine receptor complex in humans.

Flaugh in U.S. Pat. No. 4,576,959 discloses the compounds employed in the present invention as central serotonin agonists. As such, the compounds are taught to be useful in treating depression, obesity, alcoholism, smoking or senile dementia. There is no disclosure in the patent of using the compounds to treat anxiety.

The present invention relates to a method of treating anxiety. More specifically, the invention provides a method of treating anxiety in humans with a specified tetrahydrobenzindole. The activity of these compounds is believed to be based on agonist action at the 5HT-1A receptor As such, the tetrahydrobenzindoles are believed to cause fewer side affects than existing compounds.

SUMMARY OF THE INVENTION

The present invention provides a method of treating anxiety in humans comprising administering to a human susceptible to or suffering from anxiety an antianxiety dose of a compound of the formula

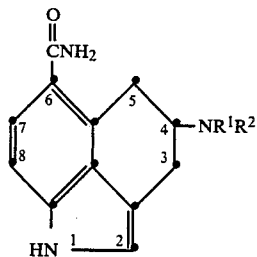

wherein:
$R^1$ is hydrogen, methyl, ethyl, n-propyl or allyl;
$R^2$ is hydrogen, methyl, ethyl, n-propyl or allyl; and
the pharmaceutically acceptable acid addition salts thereof.

DETAILED DESCRIPTION OF THE INVENTION

Pharmaceutically-acceptable acid addition salts of the compounds employed in the invention include salts derived from non-toxic inorganic acids such as: hydrochloric acid, nitric acid, phosphoric acid, sulfuric acid, hydrobromic acid, hydriodic acid, phosphorous acid and others, as well as salts derived from non-toxic organic acids such as aliphatic mono and dicarboxylic acids, phenyl-substituted alkanoic acids, hydroxyalkanoic and hydroxyalkandioic acid, aromatic acids, aliphatic and aromatic sulfonic acids. Such pharmaceutically-acceptable salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, acrylate, formate, isobutyrate, caprate, heptanoate, propiolate, oxalate, malonate, succinate, suberate, sebacate, fumarate, maleate, mandelate, butyne-1,4-dioate, hexyne-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, β-hydroxybutyrate, glycollate, malate, naphthalene-1-sulfonate, naphthalene-2-sulfonate and mesylate.

The compounds employed in the method of the present invention have an asymmetric center at the carbon atom at the 4-position of the tetrahydrobenz[c,d]indole ring. As such the compounds can exist as either the racemic mixture, or as the individual stereoisomers. Both types of compounds are contemplated for use in the method of the present invention.

The following list illustrates representative compounds suitable for use in the present invention.

(±)-4-(di-n-propylamino)-1,3,4,5-tetrahydrobenz[c,d]indole-6-carboxamide oxalate
(+)-4-amino-1,3,4,5-tetrahydrobenz[c,d]- indole-6-carboxamide maleate
(−)-4-(methylamino)-1,3,4,5-tetrahydrobenz[c,d]indole-6-carboxamide formate
(−)-4-(diethylamino)-1,3,4,5-tetrahydrobenz[c,d]indole-6-carboxamide
(+)-4-(dimethylamino)-1,3,4,5-tetrahydrobenz[c,d]indole-6-carboxamide oxalate
(+)-4-(ethylamino)-1,3,4,5-tetrahydrobenz[c,d]indole-6-carboxamide phosphate
(±)-4-amino-1,3,4,5-tetrahydrobenz[c,d]- indole-6-carboxamide hydrochloride
(±)-4-(n-propylamino)-1,3,4,5-tetrahydrobenz[c,d]indole-6-carboxamide oxalate
(±)-4-(methylamino)-1,3,4,5-tetrahydrobenz[c,d]indole-6-carboxamide toluenesulfonate
(−)-4-amino-1,3,4,5-tetrahydrobenz[c,d]- indole-6-carboxamide
(+)-4-(methylethylamino)-1,3,4,5-tetrahydrobenz[c,d]indole-6-carboxamide sulfate
(−)-4-(diethylamino)-1,3,4,5-tetrahydrobenz[c,d]indole-6-carboxamide
(−)-4-amino-1,3,4,5-tetrahydrobenz[c,d]- indole-6-carboxamide propionate
(+)-4-(dimethylamino)-1,3,4,5-tetrahydrobenz[c,d]indole-6-carboxamide
(±)-4-(diethylamino)-1,3,4,5-tetrahydrobenz[c,d]indole-6-carboxamide hydroiodide
(±)-4-amino-1,3,4,5-tetrahydrobenz[c,d]-indole-6-carboxamide
(±)-4-(ethyl-n-propylamino)-1,3,4,5-tetrahydrobenz[c,d]indole-6-carboxamide
(±)-4-(di-n-propylamino)-1,3,4,5-tetrahydrobenz[c,d]indole-6-carboxamide succinate
(−)-4-(methyl-n-propylamino)-1,3,4,5-tetrahydrobenz[c,d]indole-6-carboxamide
(+)-4-(dimethylamino)-1,3,4,5-tetrahydrobenz[c,d]indole-6-carboxamide sulfate
(−)-4-amino-1,3,4,5-tetrahydrobenz[c,d]- indole-6-carboxamide maleate
(+)-4-(diethylamino)-1,3,4,5-tetrahydrobenz[c,d]indole-6-carboxamide (+)-4-(dimethylamino)-1,3,4,5-tetrahydrobenz[c,d]indole-6-carboxamide (−)-4-(di-n-propylamino)-1,3,4,5-tetrahydrobenz[c,d]indole-6-carboxamide acetate (±)-4-amino-1,3,4,5-tetrahydrobenz[c,d]- indole-6-carboxamide succinate (±)-4-(dimethylamino)-1,3,4,5-tetrahydrobenz[c,d]indole-6-carboxamide citrate (±)-4-(di-n-propylamino)-1,3,4,5-tetrahydrobenz[c,d]indole-6-carboxamide hydrobromide (−)-4-(ethyl-n-propylamino)-1,3,4,5-tetrahydrobenz[c,d]indole-6-carboxamide benzoate (+)-4-(methyl-n-propylamino)-1,3,4,5-tetrahydrobenz[c,d]indole-6-carboxamide phthalate (+)-4-(methylethylamino)-1,3,4,5-tetrahydrobenz[c,d]indole-6-carboxamide (+)-4-(methylallylamino)-1,3,4,5-tetrahydrobenz[c,d]indole-6-carboxamide mesylate (−)-4-(di-n-propylamino)-1,3,4,5-tetrahydrobenz[c,d]indole-6-carboxamide maleate (+)-4-(diallylamino)-1,3,4,5-tetrahydrobenz[c,d]indole-6-carboxamide succinate (−)-4-amino-1,3,4,5-tetrahydrobenz[c,d]- indole-6-carboxamide fumarate (+)-4-(di-n-propylamino)-1,3,4,5-tetrahydrobenz[c,d]indole-6-carboxamide (+)-4-(diethylamino)-1,3,4,5-tetrahydrobenz[c,d]indole-6-carboxamide acetate (±)-4-(ethylamino)-1,3,4,5-tetrahydrobenz[c,d]- indole-6-carboxamide (−)-4-amino-1,3,4,5-tetrahydrobenz[c,d]- indole-6-carboxamide (+)-4-(methylamino)-1,3,4,5-tetrahydrobenz[c,d]indole-6-carboxamide (+)-4-(n-propylamino)-1,3,4,5-tetrahydrobenz[c,d]indole-6-carboxamide hydrobromide (+)-4-(di-n-propylamino)-1,3,4,5-tetrahydrobenz[c,d]indole-6-carboxamide (±)-4-(methylethylamino)-1,3,4,5-tetrahydrobenz[c,d]indole-6-carboxamide hydroiodide (+)-4-(allylamino)-1,3,4,5-tetrahydrobenz[c,d]- indole-6-carboxamide malonate (±)-4-(diethylamino)-1,3,4,5-tetrahydrobenz[c,d]indole-6-carboxamide As noted hereinbefore, the compounds employed in the method of the present invention are known. Methods of preparing the compounds, as well as pharmaceutical formulations containing the compounds, are taught by Flaugh in U.S. Pat. No. 4,576,959, herein incorporated by reference.

A preferred method of synthesizing the compounds employed in the present invention involves the reaction of a 4-substituted-6-cyano-1,3,4,5-tetrahydrobenz[c,d]indole with polyphosphoric acid. According to this procedure, typically an excess of polyphosphoric acid is combined with a 4-substituted-6-cyano-1,3,4,5-tetrahydrobenz[c,d]indole and the resulting mixture is heated to a temperature in the range of about 50° C. to about 100° C. Typically, the reaction is substantially complete after about two to eight hours, more generally about four to six hours, and the mixture is allowed to cool. The product is isolated by carefully dissolving the residual polyphosphoric acid with water or ice, and making the pH of the reaction mixture basic, preferably with sodium hydroxide. The product is extracted into a water immiscible solvent such as methylene chloride, and the solvent is evaporated from the resulting organic phase, typically under vacuum. The resulting product may be further purified, if desired, by standard techniques such as purification over solid supports such as silica gel or alumina, or crystallization from common solvents to provide a compound suitable for use in the present invention.

The following Example illustrates the synthesis of a compound employed in the present invention by the preferred procedure set forth above. The Example is not intended to be limiting to the invention in any respect and should not be so construed.

EXAMPLE 1

(±)-4-(Di-n-propylamino)-1,3,4,5-tetrahydrobenz[c,d]indole-6-carboxamide

To 30.0 g of polyphosphoric acid at a temperature of about 85° C. was added 1.5 g (5.34 mmol) of (±)-4-(di-n-propylamino)-6-cyano-1,3,4,5-tetrahydrobenz[c,d]indole. The mixture was heated at about 85° C. for five hours, cooled, and ice chips were added to the reaction mixture in order to decompose any remaining polyphosphoric acid. The mixture was diluted with water and made basic with sodium hydroxide. The mixture was extracted with methylene chloride, and the organic phase was concentrated under vacuum to dryness. The residue was chromatographed over Florisil employing methanol: methylene chloride (from 1:19 to 1:9, v:v) as the eluant. Fractions containing the major component were combined and the solvent was evaporated therefrom to provide an oil. The oil was triturated with toluene to provide crystals. The crystals were crystallized by dissolving the solid in methylene chloride:methanol (49:1, v:v), adding toluene to the solution and evaporating the solvent from the mixture after seeding with crystals. Crystals resulted after evaporation of all of the solvent. These crystals were heated in toluene and the precipitated solid was collected by vacuum filtration to provide 0.99 g of (±)-4-(di-n-propylamino)-1,3,4,5-tetrahydrobenz[c,d]indole-6-carboxamide. mp=165°–166° C.

Analysis calculated for $C_{18}H_{25}N_3O$:
Theory: C, 72.21; H, 8.42; N, 14.03;
Found: C, 72.46; H, 8.61; N, 13.80.

The present invention provides a method of treating anxiety in humans comprising administering to a human susceptible to or suffering from anxiety an antianxiety dose of a specified tetrahydrobenz[c,d]indole.

The term "antianxiety dose", as used herein, represents an amount of compound necessary to prevent or treat a human susceptible to or suffering from anxiety following administration to such human. The active compounds are effective over a wide dosage range. For example, dosages per day will normally fall within the range of about 0.005 to about 500 mg/kg of body weight. In the treatment of adult humans, the range of about 0.05 to about 100 mg/kg, in single or divided doses, is preferred. However, it will be understood that the amount of the compound actually administered will be determined by a physician, in the light of the relevant circumstances including the condition to be treated, the choice of compound to be administered, the age, weight, and response of the individual patient, the severity of the patient's symptoms, and the chosen route of administration, and therefore the above dosage ranges are not intended to limit the scope of the invention in any way. While the present compounds are preferably administered orally to humans susceptible to or suffering from anxiety, the compounds may also be administered by a variety of other routes such as the transdermal, subcutaneous, intranasal, intramuscular and intravenous routes.

The compounds employed in the invention are not believed to involve the GABA receptor system in humans. Rather, the activity of the present compounds as antianxiety agents is believed to be based upon agonist action at the 5HT-1A receptor. However, the precise mechanism by which the present compounds function is not yet known, and the present invention is not limited by any mode of operation.

The antianxiety activity of the compounds employed in the method of the present invention was established by demonstrating that the compounds increase punished responding. This procedure has been used to establish antianxiety activity in clinically established compounds.

According to this procedure, Long-Evans hooded rats (male, 400–500 g) from Charles River Laboratories, Portage, MI, were used in this study. The rats had been used for a number of drug studies prior to the present studies. The rats responded in one-hour test sessions every weekday. Responding (depressing a lever) was maintained by a multiple variable interval 30-sec, variable interval 30-sec schedule of food pellet presentation; that is, responding produced food pellets after varying time intervals, having an average value of 30 seconds. In one variable interval component, responding was not punished and rates of responding between individual animals ranged from 30–120 responses per minute. In the second variable interval component, every tenth response was punished by presentation of electric shock delivered through a grid scrambler and the grid floor of the test cage. The shock duration was 0.3 seconds, and the shock intensity was adjusted for individual rats so that the rate of punished responding was approximately 15 to 30% of the rate in the unpunished component of the multiple schedule. The animals started each day in the unpunished component signaled by illumination of a light in the test cage. After 4 minutes, this was followed by a 1-minute time-out when the cage was totally dark and responding had no consequences. The time-out was followed by a 4-minute presentation of the punished responding component signaled by a flashing cage light, and then a second 1-minute time-out period. This sequence was repeated 6 times in each weekday session. Compound effects were studied on Tuesdays and Fridays by administering various doses of the compound subcutaneously 30 minutes before the test sessions began. Vehicle injections were administered on Thursdays, and data from Thursday's sessions were used as control data to evaluate the effects of the compounds. Compound effects for each dose for each rat were calculated as a percent of the mean of the control day before and the control day after administration of each dose. The effects for particular doses were then averaged across animals, and the data were expressed as the mean±the standard error of the mean of control. This data is set forth in Table I below.

TABLE I

Punished and Unpunished Responding in Rats

| Compound | Dose (mg/kg) | Percent of Control Unpunished | Percent of Control Punished | Number of Animals |
|---|---|---|---|---|
| (±)-4-(di-n-propyl-amino)-1,3,4,5-tetra-hydrobenz[c,d]in-dole-6-carboxamide | 0.005 | 95 ± 4 | 73 ± 18 | 5 |
|  | 0.01 | 85 ± 11 | 113 ± 9 | 5 |
|  | 0.02 | 103 ± 4 | 113 ± 13 | 5 |
|  | 0.04 | 107 ± 4 | 141 ± 38 | 5 |
|  | 0.08 | 103 ± 6 | 145 ± 35 | 5 |
|  | 0.16 | 86 ± 7 | 230 ± 53 | 5 |
|  | 0.32 | 70 ± 6 | 253 ± 72 | 5 |
|  | 0.64 | 52 ± 11 | 162 ± 53 | 5 |
|  | 1.25 | 29 ± 4 | 96 ± 28 | 5 |
| (−)-4-(di-n-propyl-amino)-1,3,4,5-tetra-hydrobenz[c,d]in-dole-6-carboxamide citrate | 0.04 | 104 ± 2 | 112 ± 11 | 9 |
|  | 0.08 | 111 ± 6 | 128 ± 13 | 11 |
|  | 0.16 | 111 ± 7 | 131 ± 19 | 11 |
|  | 0.32 | 84 ± 10 | 148 ± 23 | 11 |
|  | 0.64 | 67 ± 15 | 181 ± 69 | 11 |
|  | 1.25 | 21 ± 5 | 63 ± 15 | 10 |
| (+)-4-(di-n-propyl-amino)-1,3,4,5-tetra-hydrobenz[c,d] citrate | 0.04 | 107 ± 4 | 125 ± 16 | 10 |
|  | 0.08 | 104 ± 4 | 131 ± 20 | 11 |
|  | 0.16 | 101 ± 2 | 159 ± 25 | 12 |
|  | 0.32 | 76 ± 3 | 165 ± 44 | 11 |
|  | 0.64 | 55 ± 5 | 213 ± 96 | 11 |
|  | 1.25 | 44 ± 7 | 145 ± 42 | 10 |

The data set forth in the Table establishes that the compound (±)-4-(di-n-propylamino)-1,3,4,5-tetrahydrobenz[c,d]indole-6-carboxamide, and both isomers (−)-4-(di-n-propylamino)-1,3,4,5-tetrahydrobenz[c,-d]indole-6-carboxamide citrate and (+)-4-(di-n-propylamino)-1,3,4,5-tetrahydrobenz[c,d]indole-6-carboxamide citrate, significantly increased rates of punished responding at doses which had no effect or slightly decreased rates of unpunished responding.

We claim:

1. A method of treating anxiety in humans comprising administering to a human susceptible to or suffering from anxiety an antianxiety dose of a compound of the formula

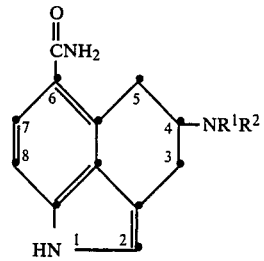

wherein:
$R^1$ is hydrogen, methyl, ethyl, n-propyl or allyl
$R^2$ is hydrogen, methyl, ethyl, n-propyl or allyl; and the pharmaceutically acceptable acid addition salts thereof.

2. A method of claim 1 wherein $R^1$ and $R^2$ are both n-propyl.

3. A method of claim 2 wherein the (+)-isomer is employed.

4. A method of claim 2 wherein the (−)-isomer is employed.

5. The method of claim 2 wherein the compound employed is (±)-4-(di-n-propylamino)-1,3,4,5-tetrahydrobenz[c,d]indole-6-carboxamide citrate.

6. The method of claim 3 wherein the compound employed is (+)-4-(di-n-propylamino)-1,3,4,5-tetrahydrobenz[c,d]indole-6-carboxamide citrate.

7. The method of claim 4 wherein the compound employed is (−)-4-(di-n-propylamino)-1,3,4,5-tetrahydrobenz[c,d]indole-6-carboxamide citrate.

* * * * *